United States Patent [19]

Parris et al.

[11] Patent Number: 4,942,259
[45] Date of Patent: Jul. 17, 1990

[54] PROCESS FOR PREPARING N-VINYL AMIDES

[75] Inventors: Gene E. Parris, Revere; John N. Armor, Orefield, both of Pa.

[73] Assignee: Air Products and Chemicals, Inc., Allentown, Pa.

[21] Appl. No.: 211,806

[22] Filed: Jun. 27, 1988

[51] Int. Cl.$^5$ ............... C07C 209/78; C07C 209/66; C07C 209/68; C07C 211/21
[52] U.S. Cl. ..................................... 564/187; 564/215
[58] Field of Search .......................... 564/215, 187

[56] References Cited

U.S. PATENT DOCUMENTS

| | | | |
|---|---|---|---|
| 3,377,340 | 4/1965 | Hartwimmer et al. | 564/215 |
| 3,531,471 | 9/1970 | Hartwimmer et al. | 260/239.3 |
| 3,914,304 | 10/1975 | Schnabel et al. | 260/561 |
| 4,018,826 | 4/1977 | Gless, Jr. et al. | 260/583 |
| 4,322,271 | 3/1982 | Jensen et al. | 204/73 |
| 4,334,097 | 6/1982 | Schmidt | 564/201 |
| 4,490,557 | 12/1984 | Dawson et al. | 564/159 |
| 4,554,377 | 11/1985 | Stackman et al. | 564/205 |
| 4,578,515 | 3/1986 | Dawson et al. | 564/215 |
| 4,670,591 | 6/1987 | Oftring et al. | 564/224 |

FOREIGN PATENT DOCUMENTS 1165638 8/1967 Fed. Rep. of Germany.
60-199685 9/1985 Japan.

*Primary Examiner*—Richard L. Raymond
*Assistant Examiner*—K. L. Konstas
*Attorney, Agent, or Firm*—Mark L. Rodgers; William F. Marsh; James C. Simmons

[57] ABSTRACT

N-vinyl amides having the general structural formula:

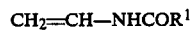

wherein $R^1$ is hydrogen, a $C_1$ to $C_6$ alkyl group or $C_6$-$C_9$ aryl or substituted aryl group, are formed by cracking carboxylic acid amides having the general structure formula:

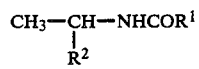

wherein $R^1$ is as described above, and $R^2$ is a $C_1$ to $C_9$ alkoxy, carboxy or carboxamide group. Said carboxylic acid amides are cracked by heating, to a temperature of about 150°–350° C., in the presence of a porous, hydrogen-abstracting catalyst.

19 Claims, No Drawings

PROCESS FOR PREPARING N-VINYL AMIDES

TECHNICAL FIELD OF THE INVENTION

The present invention relates to cracking carboxylic acid amides to form N-vinyl carboxylic acid amides.

BACKGROUND OF THE INVENTION

Several different methods have been taught in the literature to produce vinylamides. Typically these methods initially involve the formation of precursors which are subsequently pyrolyzed or cracked to yield the desired vinylamides.

U.S. Pat. No. 4,554,377 teaches a method for preparing N-vinylacetamide via the thermal pyrolysis of N-($\alpha$-methoxyethyl) acetamide at temperatures of 400° to 500° C., without using a catalyst. A similar method is taught in Japanese Patent Application 60-199685. In this method alkoxyethyl formamide derivatives are produced as precursors which are subsequently subjected to thermal decomposition to form N-vinyl formamide.

U.S. Pat. No. 4,334,097 teaches a process for the synthesis of N-vinyl amides from alkoxyethyl amides and their N-alkyl derivatives by splitting-off alcohols. The starting materials are vaporized and cracked in a furnace with porous silica at temperatures of 225°–300° C. at atmospheric or subatmospheric pressures. U.S. Pat. No. 4,322,271 describes a process in which N-vinyl-N-alkyl carboxylic acid amides are prepared by splitting-off an alcohol from the respective alkoxy precursor with or without a catalyst. The catalysts disclosed are weakly acidic catalysts, such as weakly acidic oxides of Al, Be, Zr and W; weakly acidic phosphates of Ca, Al, Mo, B and W; supported aluminosilicates in the H form; and also ammonium salts. Liquid and gas phase conditions in a temperature range of 60°–350° C. are employed.

U.S. Pat. No. 4,670,591 discloses a process for the preparation of N-$\alpha$-alkoxyethylformamides, used as precursors to N-vinylformamide. The patent also discloses preparing N-vinylformamide by the pyrolysis of the precursor over catalysts such as $SiO_2$, alumina, $Al_2O_3$, marble, iron, copper, MgO or ZnO. The pyrolysis is carried out at atmospheric or subatmospheric pressure in the temperature range of 300° to 550° C.

U.S. Pat. No. 3,914,304 discloses a process for cracking N-$\alpha$-alkoxyethyl carboxylic acid amides to form N-vinyl carboxylic acid amides, optionally in the presence of an inert gas such as $N_2$, Ar or $CO_2$. Filling bodies made from inert material such as glass, quartz, ceramics, porcelain, carbon, graphite, steel and the like are used to effect heat transfer in the reaction zone. Compressed oxides of zinc, zirconium, thorium, cerium, chromium, magnesium, aluminum and the like are also used. Additionally, U.S. Pat. No. 3,531,471 discloses preparing N-vinyl compounds by heating alkoxyalkyl amides at 50°–200° C. in the gaseous phase over weakly acidic catalysts such as oxides of Al, Be, Zr and W, phosphates of Ca, Al, B and W, and other similar compounds. Similar catalysts and/or processes for cracking alkoxyalkyl amides are disclosed in U.S. Pat. No. 3,377,340 and German patent application 1,165,638.

U.S. Pat. No. 4,578,515 discloses a process for cracking ethylidene bisformamide by heating it to a temperature in the range of from about 150° C. to 750° C., preferably 300° C. to 625° C., for from about 0.1 second to 1 hour in the presence of a solid surface catalyst. The pyrolysis is effected over a non-acidic or weakly acidic catalyst such as glass or marble chips. Other listed catalysts, which largely serve as heat transfer media, include distomaceous earth, fumed silica, chopped glass fiber, silica gel, formed sand, calcium carbonate and steel. Related disclosures which describe similar pyrolysis technology to produce N-vinylacetamide or N-vinylformamide include U.S. Pat. Nos. 4,490,557 and 4,018,826.

BRIEF SUMMARY OF THE INVENTION

The present invention is a process for forming N-vinyl amides having the general structural formula:

$$CH_2=CH-NHCOR^1$$

wherein $R^1$ is hydrogen, a $C_1$ to $C_6$ alkyl group or a $C_6$–$C_9$ aryl or substituted aryl group, by cracking; i.e. heating, carboxylic acid amides having the general structure formula:

$$CH_3-\underset{R^2}{\underset{|}{CH}}-NHCOR^1$$

wherein $R^1$ is as defined above, and $R^2$ is a $C_1$ to $C_9$ alkoxy, carboxy or carboxamide group.

Such carboxylic acid amides are heated in or near the gaseous state to a temperature of about 150°–350° C. in the presence of a porous, hydrogen-abstracting catalyst.

The present process achieves high conversions and high selectivities for said N-vinyl amides at relatively low temperatures at which hydrogen cyanide by-product production is low. Unlike typical prior art cracking processes, the present process can, optionally, be run at atmospheric or higher pressures, which increases the mean free path of molecules allowing more catalyst to be utilized and thereby achieving higher space/time yields relative to such other processes. Additionally, it has been demonstrated that the present process achieves good cracking results when using either single or co-feedstocks. In contrast to prior art teachings on the thermal pyrolysis of vinyl amides, the present process affords higher space/time yields, lower preferred temperatures and the ability to operate at atmospheric pressure. Traditional cracking processes typically involve C—C bond breakage. The present process, however, involves the catalytic breakage of a C-X bond where X is typically compounds of O or N, or possibly F, S, P or Si. The cracking process of the present invention can be described as a vinylidine cracking reaction illustrated by the following equation:

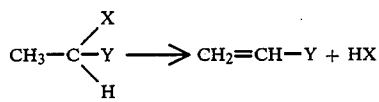

where X=O, N, S, F, P or Si.

In one embodiment the present invention provides a process for cracking ethylidene bis(formamide) to form N-vinyl formamide, a monomer which is used to form a precursor polymer for the production of poly-(N-vinylamine).

DETAILED DESCRIPTION OF THE INVENTION

The present invention is a process for producing N-vinyl amides which affords substantially improved activity and/or selectivity in the cracking of carboxylic acid amides which are vinylamide precursors. Carboxylic acid amides having the general structural formula:

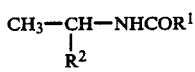

wherein $R^1$ is hydrogen, a $C_1$ to $C_6$ alkyl group or a $C_6$–$C_9$ aryl or substituted aryl group, and $R^2$ is a $C_1$ to $C_9$ alkoxy, carboxy or carboxamide group, are heated to a temperature of about 150°–350° C. in the presence of a porous, hydrogen-abstracting catalyst, to produce N-vinyl amides having the structural formula:

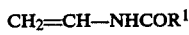

wherein $R^1$ is as described above.

Examples of specific carboxylic acid amides which are useful in this process include: ethylidene bis(formamide) (BIS), N-(1-methoxyethyl) formamide (MEF), N-(1-ethoxyethyl)formamide (EEF), N-(1-acetoxyethyl) formamide (AEF), N-(1-methoxyethyl)acetamide (MEA) and N-(1-ethoxyethyl) acetamide (EEA).

For the purpose of this invention, selectivity is defined as moles of desired product produced per moles of reactant consumed with the quotient multiplied by 100, and conversion is defined as moles of reactant consumed per moles of reactant fed with the quotient multiplied by 100. Yield is selectivity×[conversion/100].

The catalysts suitable for the cracking process are porous, hydrogen abstracting catalysts, such as activated carbon, magnesium oxide, silicon phosphate prepared by calcining $H_3PO_4/SiO_2$ at 800°–900° C., strontium pyrophosphate, neutral or basic calcium hydroxyapatite, $CuCrO_2$ and $La_2O_3$, with preferred catalysts being activated carbon, neutral or basic phosphates, $CuCrO_2$ and magnesium oxide. The catalytic cracking reaction is carried out at a temperature in the range of about 150° to 350° C., with a temperature from 200° to 350° C. being preferred. Best product selectivities are obtained when the process is operated at low partial pressure of the organic feed to ensure that gas phase is predominant, since, although the reaction can take place in the liquid phase, the gas phase is preferred. Even when operating in the gas phase however, capillary condensation in the catalyst pores is typical. Total pressures in the range of about 3 torr to about 3000 torr or higher are applicable, however, total pressures up to about 1000 torr are preferred and provide the highest product selectivity. Such conditions enable rapid transport of the cracked, gaseous product to external cooling traps, where it is condensed and collected, thus preventing degradation.

As stated above, an activated form of carbon is a preferred catalyst for the present reaction. Activated carbon is distinguishable from other forms of carbon, in that it is principally elemental carbon, the surface of which may be partially oxidized or reduced, and which is characterized in that is has an extremely large surface area with a microporous structure. In some instances, a carbonaceous layer may be formed in-situ from the decomposition of the organic reactants on the surface of the cracking catalyst. This carbonaceous layer may then serve as an activated carbon-type catalyst for the vinylidine cracking reaction.

Optionally, the reaction may be carried out in the presence of an inert gas diluent, such as helium, nitrogen, argon, or mixtures thereof. Such inert diluents are beneficial in that they serve to achieve low carboxylic acid amide partial pressures in the reactor, increase the heat transfer to and from the catalyst bed, decrease the mean free path of the molecules allowing better mass transport into the catalyst particles and pores, and in some instances eliminate the need for using an expensive vacuum process. The main purpose for using a diluent in the present process is to maintain a low organic amide partial pressure, whereas prior art teachings use diluents only as a sweep to prevent reactor plugging or to aid in transfer of material to the reactor. Since the inert diluent decreases the feed partial pressure of the carboxylic acid amide, the cracking reaction can be carried out at atmospheric or other pressures as indicated above and still be in the gas phase, since it is the carboxylic acid amide partial pressure which must be low in order to maintain a predominantly gas phase reaction. Preferably the inert gas is added in an amount of about 20–98 mol % based on total feed (inert and organic). While helium exhibits the best thermal conductivity, nitrogen is the least expensive and generally the preferred diluent. The use of a diluent is only a preferred embodiment however, and the reaction can be run without, although, depending on the other reaction conditions, a vacuum may be necessary to maintain a predominantly gas phase reaction. In addition, it is useful to purge the oxygen from the organic amide before the amide is fed to the catalyst. This tends to prolong catalyst life and maximize catalyst productivity.

The carboxylic acid amide to be cracked can be used in its substantially pure form, or as a crude mixture as obtained in its synthesis. Additionally, it may be diluted with a suitable functionally inert solvent, such as water, ethanol, formamide (FAM), dimethyl sulfoxide (DMSO) and the like. The reaction may be carried out in either a batch phase or continuous mode. For continuous (flow reactor) processes, residence times for the total feed is typically from about 0.01 seconds to 20 mins., while residence times of several hours can be used for batch reactors. Preferred residence times for the flow reaction, however, range from about 0.01 to about 2.0 seconds. Trace amounts of phenothiazine or similar compounds may be added to the condensed liquid products to inhibit free radical initiated reactions of the vinyl monomer product.

Since it has been demonstrated that only certain catalysts show significant improvement for cracking N-vinyl amide precursors, a cracking index was developed to identify and group the materials which exhibit such improved catalytic properties. Furthermore, although the catalysts which exhibit these improved properties can all be classified as porous, hydrogen-abstracting materials, the details of the mechanism by which such improvement takes place are not yet fully understood. It has been found, however, as shown in Table A below, that all of the catalysts which exhibit improved catalytic properties for cracking carboxylic acid amides, such as about 70% selectivity and up to 100% conversion for cracking BIS, consistently afford high values, i.e., about 200 or greater, of the index as defined using test reactions with other vinyl forming reactants. Materials which do not exhibit these improved catalytic properties, afford low values of the cracking index; i.e., less than about 200.

The vinyl-forming reactants that were used to develop the cracking index are diethylacetal (Acetal) which produces ethylvinylether (EVE) and ethanol, and methyl-tertiarybutylether (MTBE) which produces isobutylene and methanol. At acetal conversions of greater than 50%, it was found that the preferred catalysts afford both moderate-high EVE selectivity and low MTBE conversions. Thus, the index is defined as follows:

$$\text{Cracking Index} = \frac{\% \text{ Acetal conversion}}{\% \text{ MTBE conversion}} \times \% \text{ EVE selectivity}$$

A few examples help to illustrate the discrimination process built into the index. A comparison between Darco carbon (activated carbon) and $TiO_2$ catalysts in Table A show that both catalysts afford high Acetal conversions. However, although the MTBE conversion is only slightly lower, the EVE selectivity is substantially higher for Darco carbon than $TiO_2$. Thus, activated carbon is a preferred catalyst and $TiO_2$ is not. Also, a comparison between calcium hydroxyapatite, Ca/P ratio=2.2 (CaHAP-2.2) and $TiO_2$ is instructive. In this case the EVE selectivity is comparable for both catalysts. However, the $TiO_2$ catalyst that affords this moderate EVE selectivity also causes a 2-fold higher MTBE conversion thereby making it an inferior catalyst to CaHAP-2.2 for the reaction of the present invention. Both the activated carbon and CaHAP-2.2 catalysts are shown to yield high NVF selectivities for cracking BIS whereas $TiO_2$ does not. The cracking index for several catalysts are shown in Table A below.

TABLE A

Development of an Index to Rank Catalytic Cracking Efficiency.[a]

| Catalyst | Catalyst (gms) | % Conv. Acetal | % Conv. MTBE | % EVE[c] Select. | Cracking[d] Index | % NVF[e] (2 hr) | % NVF[f] (4 hr) |
|---|---|---|---|---|---|---|---|
| MgO | 0.1541 | 74.5 | 11.3 | 98.4 | 648.3 | 94 | 97 |
| Darco Carbon | 0.0106 | 92.9 | 24.7 | 90.1 | 339.4 | 76 | 89 |
| CaHAP-2.2 | 0.0315 | 95.6 | 18.8 | 66.5 | 338.6 | 87 | 99 |
| $TiO_2$[b] | 0.1995 | 98.0 | 39.1 | 62.3 | 156.0 | 36 | 46 |
| gamma-$Al_2O_3$ | 0.0210 | 99.4 | 92.2 | 16.5 | 17.8 | 40 | 60 |
| 13% AS[g] | 0.0139 | 99.8 | 99.3 | 6.2 | 6.2 | 15 | 33 |

[a]Reactions conducted in the glass injector liner of a HP 5890 gas chromatograph. The indicated wt of catalyst was loaded into the liner and two 2 uL injections made at 250° C. and 8 psi column head pressure. A DB-5 30 m capillary column was used and the split ratio was 145 to 1.
[b]$TiO_2$ catalyst is Ti3401 from Pflatz & Bauer. Surface Area (SA) = 81 m2/g.
[c]mole % selectivity = (moles EVE produced/moles Acetal consumed)(100). Average of two injections. EVE = ethylvinylether.
[d]Cracking Index = (% Acetal Conversion/% MTBE conversion)(% EVE selectivity).
[e]% NVF from BIS after 2 hrs time-on-stream in flow reactor.
[f]% NVF from BIS after 4 hrs time-on-stream in flow reactor.
[g]Davison grade 980-13 alumina/silica. SA = 375 m2/g.

The cracking index set out in Table A above clearly shows that catalysts which show improved properties for cracking carboxylic acid amides have high cracking index values, whereas catalysts which do not show such improved properties, have low cracking index values. It was determined through extrapolation that, catalysts which show improved cracking properties will have a cracking index value of about 200 or greater.

Several examples were carried out in accordance with the present invention. These examples are presented to better illustrate the present invention and are not meant to be limiting.

EXAMPLE 1

A 5.5 cc sample of Darco TM activated carbon, lot no. 0909BJ, having a cracking index value of about 339, was crushed and sieved into 24-32 mesh and loaded into a ½" diameter stainless steel tubular flow reactor. A catalyst pre-bed consisting of about 9 cc of 10-16 mesh quartz chips was added to the reactor. The reactor was placed in a conventional tube furnace such that the catalyst bed was uniformly heated. The catalyst was evacuated to 21 torr and heated to 252° C. under a flow of 20 SCCM $N_2$.

Purified ethylidene bisformamide (BIS), a solid at room temperature, was heated to 120°-130° C. in a 175 cc stainless steel cylinder and the liquid transferred to an ISCO stainless steel piston pump under $N_2$ pressure. The heated liquid was then pumped to the reactor at 4.6 cc/hr through a dome-loaded back pressure regulator (BPR) set at 100 psig. The reactor effluent, comprising the products of cracking and $N_2$ at 21 torr, was cooled by passing through a coiled tube immersed in cool water and collected in a round bottom flask immersed in ice. The composition of the liquid product was determined by gas chromatography after adding 1 g product to 9 g methanol and 0.15 g N-ethylpiperidine, the latter acting as an internal standard. The above conditions resulted in 98% conversion of the BIS feed, on the basis of which 100 mol. % selectivity to N-vinyl formamide (NVF) was obtained.

EXAMPLE 2

A second run was carried out in accordance with the general procedures set out in Example 1 above, using a 1.0 cc sample of the Darco activated carbon with 0.25 cc quartz chips pre-bed heated to 234° C. under 25 SCCM $N_2$ at 21 torr pressure. The liquid, purified BIS feed was established at 9.8 cc/hr. Analysis of the reactor effluent showed 73% conversion of BIS and 73 mole % selectivity of the converted BIS to NVF.

EXAMPLE 3

A 1.0 cc sample of the same Darco activated carbon used above was heated to 243° C. under 240 SCCM of $N_2$ at 1020 torr pressure, in accordance with the procedure set out in Example 1 above. A BIS feed rate of 10.0 cc/hr was used. Analysis of the reactor effluent showed 96% BIS conversion with 41 mole % NVF selectivity.

EXAMPLE 4

Three additional runs (runs 4, 5, and 8) were carried out in accordance with the general procedures set out in Example 1 above along with two comparative runs, 6 and 7. Conversions and product selectivities for cracking pure BIS over various catalysts at various reaction conditions were measured. The residence time for each run ranged from 0.14 to 0.17 sec. All runs were carried out in a flow reactor. Run 4 was carried out using Norit carbon, a commercially available activated carbon which has similar properties and characteristics to Darco activated carbon used in Examples 1-3 above. Additionally, run 1 from Example 1 is also reproduced in Table 1 to illustrate the advantages of operating at lower partial pressures of the amide, since under similar conditions the Norit and Darco carbons would give similar results. The specific reaction conditions along with the results of each run are set out in Table 1 below.

TABLE 1

Cracking of Pure BIS Feed Over Catalysts in a Flow Reactor

| Run | Catalyst | Temp. (°C.) | Press. (torr) | BIS Flow[a] (cc/hr) | $N_2$ Flow (SCCM) | % BIS Conv. | % NVF[b] Select. |
|---|---|---|---|---|---|---|---|
| 1 | Darco Carbon | 252 | 21 | 4.6 | 20 | 98 | 100 |
| 4 | Norit Carbon[c] | 248 | 1070 | 9.6 | 246 | 85 | 37 |
| 5 | 6% $PO_4/SiO_2$[d] | 230 | 970 | 5.0 | 285 | 71 | 83 |
| 6 | gamma-$Al_2O_3$[e] (comparative) | 244 | 970 | 5.0 | 245 | 95 | 51 |
| 7 | alpha $Al_2O_3$[f] (comparative) | 242 | 20 | 4.5 | 20 | 77 | 64 |
| 8 | $Sr_2P_2O_7$[g] | 248 | 20 | 4.3 | 4 | 88 | 98 |

[a]BIS purity: 90% for runs 4, 5, 6, 8; and 95% for run 7.
[b]mole % selectivity = (moles NVF produced/moles BIS consumed) × 100
[c]Nordit ROX 0.8 granular activated carbon, SN A-5672; surface area = 900 m2/g, pore volume = 1.0 cc/g.
[d]$H_3PO_4$/silica gel, heat treated in air at 850° C.; Analysis: 1.97 wt % P, 42.3 wt % Si.
[e]Conoco Catapal TM SB alumina extrudates, Lot No. 136J131-2C, heat treated in air at 500° C.; SA = 211 m2/g.
[f]Alcoa T-64 TAB alumina, surface area = 0.04 m2/g.
[g]APCI Paulsboro SrHPO4, Lot 85-1, heat treated in $N_2$ at 410° C.; SA = 16 M2/g.

EXAMPLE 5

A 1.0 cc sample of the 24–32 mesh Darco activated carbon described in Example 1 was loaded in a ¼″ diameter, 316 SS tubular reactor with a pre-bed of 10–16 mesh quartz chips. The reactor was evacuated to 20 torr and heated to 232° C. under 4.5 SCCM $N_2$ flow. A crude BIS mixture, obtained as a liquid in the synthesis of BIS from acetaldehyde and formamide as described in U.S. Pat. No. 4,578,515A, was pumped from an ISCO piston pump to the reactor at a feed rate of 10.7 cc/hr. The crude BIS comprised 22% BIS, 58% formamide, 7.5% acetic acid, 0.6% formic acid, 1.3% ammonium formate, and 3.6% water. The composition of the cracked product obtained showed that 79% of the contained BIS was converted to products with 55% selectivity to NVF. The temperature of the reactor was then increased to 251° C. while maintaining all other variables constant. At the higher temperature of 251° C. the BIS conversion increased to 86% and the NVF selectivity also increased to 65%.

EXAMPLE 6

5 cc of Darco activated carbon was loaded into the reactor as in Example 1. After heating to 273° C. under 19 torr pressure and 4 SCCM $N_2$, a crude BIS feed, as described in Example 5 above, of 10.0 cc/hr was started. The conversion of the BIS was 100% and 93% selectivity to NVF was obtained.

EXAMPLE 7

A series of additional runs was carried out in accordance with the general procedures set out in the above examples to crack a crude BIS feed in a flow reactor. Various catalysts and reaction conditions were used for these runs and are reported, along with the conversions and selectivities in Table 2 below.

TABLE 2

Cracking of Crude BIS Feed Over Catalysts in a Flow Reactor

| Run | Catalyst | Temp. (°C.) | Press. (torr) | BIS Flow[a] (cc/hr) | $N_2$/He (SCCM) | Residence[b] Time (sec) | % BIS Conv. | % NVF[c] Select. |
|---|---|---|---|---|---|---|---|---|
| 11 | Darco Carbon[d] | 252 | 21 | 4.80 | 3 | 0.110 | 100 | 76 |
| 12 | Darco Carbon[d] | 249 | 150 | 9.80 | 5 | 0.080 | 89 | 49 |
| 13 | Darco Carbon[d] | 301 | 175 | 18.00 | 3 | 0.050 | 97 | 63 |
| 14 | Darco Carbon[d] | 323 | 175 | 17.70 | 3 | 0.050 | 96 | 83 |
| 15 | Darco Carbon[d] | 275 | 860 | 3.84 | 930 | 0.038 | 84 | 90 |
| 16 | Darco Carbon[d] | 275 | 860 | 30.00 | 0 | 0.130 | 90 | 7 |
| 17 | Norit Carbon[e] | 275 | 860 | 30.00 | 0 | 0.130 | 90 | 7 |
| 18 | Norit Carbon[e] | 275 | 860 | 10.00 | 290 | 0.090 | 86 | 38 |
| 19 | Darco Carbon[d] | 150 | 860 | 10.00 | 0 | [f] | 0 | 0 |
| 20 | Darco Carbon[d] | 175 | 860 | 10.00 | 0 | [f] | 28 | 40 |
| 21 | Darco Carbon[d] | 210 | 860 | 10.00 | 0 | [f] | 58 | 34 |
| 22 | Darco Carbon[d] | 250 | 860 | 10.00 | 0 | 1.250 | 93 | 11 |
| 23 | Darco Carbon[d] | 300 | 860 | 10.00 | 0 | 1.150 | 97 | 13 |
| 24 | 6% $PO_4/SiO_2$[g] | 304 | 175 | 20.00 | 4 | 0.040 | 90 | 36 |
| 25 | 2% $PO_4/SiO_2$[h] | 275 | 860 | 10.00 | 290 | 0.090 | 74 | 40 |
| 26 | Darco Carbon[d] | 275 | 860 | 8.00 | 600 | 0.110 | 94 | 91 |
| 27 | Darco Carbon[d,i] | 325 | 860 | 8.00 | 600 | 0.110 | 99 | 89 |

TABLE 2-continued

Cracking of Crude BIS Feed Over Catalysts in a Flow Reactor

| Run | Catalyst | Temp. (°C.) | Press. (torr) | BIS Flow[a] (cc/hr) | N2/He (SCCM) | Residence[b] Time (sec) | % BIS Conv. | % NVF[c] Select. |
|---|---|---|---|---|---|---|---|---|
| 28 | MgO[j] | 275 | 860 | 4.00 | 600 | 0.120 | 97 | 97 |

[a]Feed Composition: 22% BIS, 58% FAM, 7.5% HOAc, 0.6% HCOOH, 1.3% NH4HCOO, 3.6% H2O, and oligomers.
[b]Residence Time (sec) = (3600*P*Vb)/(N*R*T), where P and T(K) are experimental values, N is the molar hourly flow rate, Vb is the volume of catalyst as 24–32 mesh, and R is the gas constant.
[c]mole % selectivity = (moles NVF produced/moles BIS consumed)(100).
[d]Darco granular activated carbon, Lot No. 0909BJ; surface area - 600 m2/g.
[e]Norit ROX 0.8 granular activated carbon, SN A-5672; surface area = 900 m2/g, pore volume = 1.0 cc/g.
[f]Residence Time = 18.8 mins if liquid phase assumed.
[g]H3PO4/silica gel, heat treated in air at 850° C.; Analysis: 1.97 wt % P, 42.3 wt % Si.
[h]H3PO4/silica gel, heat treated in air at 850° C.; Analysis: 0.69 wt % P, 42.7 wt % Si.
[i]Crude BIS feed purged with and maintained under N2 atmosphere.
[j]Calgon Maglite TM CG11, SN R-1970, granular MgO; surface area = 30 m2/g, pore volume = 0.21 cc/g.

From the results reported in Table 2 above, it can be seen that the porous catalysts of the present invention are useful for cracking BIS at low temperatures; i.e. less than 350° C. It can also be seen, however, that reaction conditions, such as temperature, feed pressure, amide (BIS) partial pressure, etc. have a marked effect on the reaction. Specifically, runs in which a predominant liquid phase was believed to be present (runs 19–21), and those in which BIS partial pressure was relatively high e.g. runs 16 and 17, showed the poorest results. Run 19 which was run under the least desirable reaction conditions did not show any BIS conversion, although it is believed that a longer reaction time would have resulted in some conversion to NVF.

EXAMPLE 8

Additional cracking runs 29 to 41 were carried out using a diluted BIS feed in a flow reactor over various porous catalysts at a variety of reaction conditions. Also, ten comparative runs, runs 42 to 51, were carried out using various prior art catalysts. The specific catalysts and conditions, as well as the results, are reported in Table 3 below.

TABLE 3

Cracking of Dilute BIS Feed Over Catalysts in a Flow Reactor[a]

| Run | Catalyst | Temp. (°C.) | BIS Flow[b] (cc/hr) | N2/He (SCCM) | Residence[c] Time (sec) | % BIS Conv. | % NVF[d] Select. |
|---|---|---|---|---|---|---|---|
| 29 | Darco Carbon[e] | 275 | 18.0 | 900 | 0.073 | 100 | 89 |
| 30 | MgO[f] | 275 | 18.0 | 900 | 0.073 | 91 | 98 |
| 31 | MgO[g] | 275 | 8.0 | 600 | 0.109 | 97 | 93 |
| 32 | Darco Carbon | 400 | 54.0 | 900 | 0.046 | 100 | 74 |
| 33 | Darco Carbon | 300 | 2.8 | 210 | 2.000 | 100 | 54 |
| 34 | Calgon-APC[i] | 275 | 4.0 | 600 | 0.120 | 100 | 84 |
| 35 | Super-A[j] | 275 | 4.0 | 600 | 0.220 | 100 | 91 |
| 36 | MgO[f] | 325 | 54.0 | 900 | 0.052 | 94 | 93 |
| 37 | MgO[g] | 325 | 36.0 | 600 | 0.074 | 94 | 94 |
| 38 | MgO[g] | 275 | 36.0 | 600 | 0.080 | 80 | 79 |
| 39 | MgO[k] | 275 | 4.0 | 600 | 0.120 | 100 | 88 |
| 40 | CuCrO2[l] | 275 | 4.0 | 600 | 0.120 | 100 | 91 |
| 41 | La2O3 | 275 | 18.0 | 900 | .073 | 88 | 81 |
| 42 | ZnO | 275 | 18.0 | 900 | 0.073 | 82 | 72 |
| 43 | ZrO2 | 275 | 14.0 | 900 | 0.073 | 79 | 65 |
| 44 | 13% SiO2/Al2O3 | 275 | 4.0 | 600 | 0.120 | 93 | 37 |
| 45 | TiO2 | 275 | 18.0 | 900 | 0.073 | 97 | 46 |
| 46 | SiO2 gel | 275 | 18.0 | 900 | 0.073 | 86 | 62 |
| 47 | Cr2O3/Al2O3[m] | 275 | 4.0 | 600 | 0.120 | 100 | 44 |
| 48 | Ni/support[n] | 275 | 4.0 | 600 | 0.120 | 100 | 62 |
| 49 | g-Al2O3[o] | 275 | 4.0 | 600 | 0.120 | 100 | 30 |
| 50 | Na2O/g-Al2O3[p] | 275 | 4.0 | 600 | 0.120 | 100 | 28 |
| 51 | LZY52[q] | 275 | 8.0 | 600 | 0.110 | 97 | 77 |

[a]Reactor Pressure = 850–900 torr.
[b]Feed Composition: 22% BIS, 78% FAM; purged with and maintained under N2 atmosphere.
[c]Residence Time (sec) = (3600*P*Vb)/(N*R*T), where P and T(K) are experimental values, N is the molar hourly flow rate, Vb is the volume of catalyst as 10–16 mesh, and R is the gas constant.
[d]mole % selectivity = (moles NVF produced/moles BIS consumed)*100. Values given after 4 hrs. on stream.
[e]Darco granular activated carbon, Lot No. 0909BJ; surface area - 600 m2/g.
[f]Harshaw MgO, MG-0601 T ⅛", S.N. 407A-20-2-10, SA = 25 m2/g.
[g]Calgon granular MgO, Maglite CG11, SN 4-1970, SA = 30 m2/g.
[i]Calgon activated carbon. Type: APC 12 × 40. SA = 1525 m2/g
[j]Amoco Super-A carbon, Lot 79-9, sample 332GX31, SA = 3000 m2/g.
[k]Calgon granular MgO, Maglite CG10, SN R-1813, SA = 190 m2/g.
[l]Harshaw copper chormite catalyst. Cu-1808 T ⅛", Lot 5, SA = 30 m2/g.
[m]Harshaw chromia alumina catalyst, Cr-0304 T ⅛", E-175-1-2-3, SA = 62 m2/g.
[n]Harshaw nickel catalyst, Ni-1404 T 3/16", Spec. 103, Lot 332, SA = 125 m2/g.
[o]Catapal alumina ⅛" extrudates, Lot 136J131-2C, calcined at 500 C, SA = 211 m2/g.
[p]See [o] above; then impregnated with NaNO3 solution and calcined at 600 C to give 0.23 wt % Na.
[q]Linde LZY-52 zeolite, Lot 9680801014. Selectivity at 2 h on stream = 45%.

The results reported in Table 3 above clearly show that the catalysts of the present invention consistently give superior results than the prior art catalysts used in the comparative examples. Additionally it should be noted that the run using a zeolite catalyst, run 51, showed that selectivity to NVF improved over time, unlike the activated carbon or MgO catalysts which exhibited high activity and high selectivity from the onset. In addition, $ZrO_2$, $TiO_2$ and gamma $Al_2O_3$ also showed improved selectivity (although <70%) with extended time on stream. This is believed to be an indication of in-situ carbonaceous deposits which also serve as catalysts.

EXAMPLE 9 (COMPARATIVE)

A run was carried out to compare the performance of the catalysts of the present invention with the performance of quartz chips (a catalyst taught in the prior art) for cracking a crude BIS feed in a flow reactor. The general experimental procedure as used in Example 5 above, was carried out for the run using quartz chips. The same procedure and reaction conditions were used as for run 11 as reported in Table 2 above using Darco Carbon. The specific conditions, along with the results for the run using quartz chips are set out in Table 4 below. For ease of comparison, the results for Darco Carbon are also reproduced in Table 4.

tions as run 31 (MgO catalyst) in Table 3 above. To show the comparison at higher temperatures; i.e. 400° C., run 55 using quartz chips was carried out under the same conditions as run 32 using Darco Carbon. Run 56 using quartz chips was carried out under the same conditions as run 20 using Darco Carbon in Table 2 above for cracking a crude BIS feed. Finally, run 57 was carried out using a empty tube; i.e.; no catalyst. The results of these comparative runs are set out in Table 5 below.

TABLE 5

Cracking of Dilute BIS Feed Over Catalysts in a Flow Reactor

| Run | Catalyst | Temp. (°C.) | BIS Flow[a] (cc/hr) | N2/He (SCCM) | Residence[c] Time (sec) | % BIS Conv. | % NVF[d] Select. |
|---|---|---|---|---|---|---|---|
| 29 | Darco Carbon[e] | 275 | 18.0 | 900 | 0.073 | 100 | 89 |
| 30 | MgO[f] | 275 | 18.0 | 900 | 0.073 | 91 | 98 |
| 53 | Quartz Chips[h] | 275 | 18.0 | 900 | (.073) | 31 | 72 |
| 31 | MgO[g] | 275 | 8.0 | 600 | 0.109 | 97 | 93 |
| 54 | Quartz Chips | 275 | 8.0 | 600 | (.109) | 51 | 83 |
| 32 | Darco Carbon | 400 | 54.0 | 900 | 0.046 | 100 | 74 |
| 55 | Quartz Chips | 400 | 54.0 | 900 | (.046) | 97 | 100 |
| 20 | Darco Carbon | 175 | 10.0[b] | 0 | [i] | 28 | 40 |
| 56 | Quartz Chips | 175 | 10.0[b] | 0 | [i] | 2 | 24 |
| 57 | Empty Tube (No Catalyst) | 275 | 18.0 | 900 | — | 26 | 60 |

[a]Feed Composition: 22% BIS, 78% FAM; purged with and maintained under N2 atmosphere.
[b]Feed Composition: 22% BIS, 58% FAM, 0.6% HCOOH, 1.3% NH4HCOO, 3.6% H2O, and oligomers.
[c]Residence Time (sec) = (3600*P*Vb)/(N*R*T), where P and T(K) are experimental values, N is the molar hourly flow rate, Vb is the volume of catalyst as 10–16 mesh, and R is the gas constant.
[d]mole % selectivity = (moles NVF produced/moles BIS consumed) × 100. Values given after 4 hrs. on stream.
[e]Darco granular activated carbon, Lot No. 0909BJ; surface area - 600 m2/g.
[f]Harshaw MgO, MG-0601 T ⅛", S.N. 407A-20-2-10, SA = 25 m2/g.
[g]Calgon granular MgO, Maglite CG11, SN 4-1970, SA = 30 m2/g.
[h]19.2 gms quartz chips, 10–16 mesh. Residence times given based on a 2 cc quartz bed only.
[i]Residence time = 18.8 min. if liquid phase assumed.

The results reported in Table 5 above show that, under various sets of reaction conditions, the preferred prior art catalysts are consistently inferior to the catalyst of the present invention, and in fact show that the quartz chips show little improvement over an empty tube. A comparison of runs 32 and 55 show that, when the reaction is run at higher temperatures, the catalysts of the present invention no longer show improved results. This is believed to be due to secondary reactions of the product occurring over the catalyst at the elevated temperatures.

TABLE 4

Cracking of Crude BIS Feed Over Catalysts in a Flow Reactor

| Run | Catalyst | Temp. (°C.) | Press. (torr) | BIS Flow[a] (cc/hr) | N2/He (SCCM) | Residence[b] Time (sec) | % BIS Conv. | % NVF[c] Select. |
|---|---|---|---|---|---|---|---|---|
| 11 | Darco Carbon[d] | 252 | 21 | 4.80 | 3 | 0.110 | 100 | 76 |
| 52 | Quartz Chips | 256 | 21 | 5.00 | 3 | 0.110 | 25 | 87 |

[a]Feed Composition: 22% BIS, 58% FAM, 7.5% HOAc, 0.6% HCOOH, 1.3% NH4HCOO, 3.6% H2O, and oligomers.
[b]Residence Time (sec) = (3600*P*Vb)/(N*R*T), where P and T(K) are experimental values, N is the molar hourly flow rate, Vb is the volume of catalyst as 24–32 mesh, and R is the gas constant.
[c]mole % selectivity = (moles NVF produced/moles BIS consumed)*100.
[d]Darco granular activated carbon, Lot No. 0909BJ; surface area = 600 m2/g.

The above results clearly show that, under these reaction conditions, the Darco Carbon catalyst resulted in significantly higher BIS conversions than the preferred prior art quartz chips.

EXAMPLE 10 (COMPARATIVE)

To further demonstrate the advantage of the present catalyst over those disclosed in the prior art, several other comparative runs were carried out. A run was carried out (run 53) using quartz chips catalyst under the same reaction conditions as runs 29 and 30 in Table 3 above for Darco Carbon and MgO respectively for cracking diluted BIS feed. A second run using quartz chips (run 54) was carried out under the same condi-

EXAMPLE 11

Several runs were carried out (runs 58 to 65) in accordance with the general procedures set out in Example 5 above. The reactions were carried out in the presence of either MgO or Darco Carbon catalysts, having cracking index values of about 648 and 339 respectively, using a BIS/H2O feed. The use of water, rather than formamide, as an alternative solvent for BIS, a solid, allows greater flexibility for the feed. For example, at ambient temperature a 44.5 wt % feed solution of BIS in water was readily obtained whereas only about 22 wt % BIS can be dissolved in formamide at this temperature. This allows increased reactor productivity and reduced storage. Also, formamide and NVF are difficult to separate, and hence the use of water reduces the quantity of formamide in the product NVF and, therefore, the number of plates required in any separation scheme.

The reactions were carried out at a pressure of 800 to 900 torr. A feed containing 41.9 to 44.5% BIS in water and having a BIS purity of 99.6% was purged with and maintained under $N_2$ atmosphere. Two comparative runs (runs 66 and 67) were also carried out in accordance with the above procedures. Comparative run 66 employed Davison grade 980-13 alumina/silica, having a surface area of 375 $m^2/g$, and comparative run 67 employed gamma-$Al_2O_3$. The reaction conditions and results of runs 58 to 67 are reported in Table 6 below.

Ca/P ratio of 1.67 is the neutral point for CaHAP catalysts, and such catalysts with ratios below this level are not well suited for this process. The catalyst charge was 2.0 cc, 10–16 mesh. The reactor pressure was maintained at about 800–900 torr, and the feed was purged with and maintained under $N_2$ atmosphere. For comparison, run 74 was carried out using Davison grade 980-13 alumina/silica (cracking index value=6.2). Specific reaction conditions and results are set out in Table 7 below.

TABLE 7

Cracking of BIS to NVF Using BIS/FAM Feeds[a]

| Run | Catalyst[b] | Temp. (°C.) | BIS/FAM[c] (mL/hr) | N2/He (SCCM) | % BIS Conv. | % NVF[d] Select. |
|---|---|---|---|---|---|---|
| 68 | CaHAP-1.59[e] | 275 | 18 | 900 | 97 | 51 |
| 69 | CaHAP-1.8[e] | 275 | 18 | 900 | 97 | 97 |
| 70 | CaHAP-2.2[e] | 275 | 18 | 900 | 96 | 99 |
| 71 | MgO | 250 | 24 | 900 | 85 | 92 |
| 72 | MgO | 275 | 18 | 900 | 93 | 97 |
| 73 | MgO | 210 | 10 | 500 | 86 | 67 |
| 74 | 13% AS[f] | 250 | 18 | 600 | 94 | 33 |

[a]Reactor Pressure = 800–900 torr. BIS purity = 99.6%; feed purged with and maintained under N2 atmosphere.
[b]Catalyst charge was 2.0 cc, 10-16 mesh, in 9/16" OD 316 ss reactor tube for all runs except run 69.
[c]Feed = 20.0 wt % BIS in FAM.
[d]mole % selectivity = (moles NVF produced/moles BIS consumed) × 100. Values given after 4 hrs on stream.
[e]Calcium hydroxyapatite, Ca/P ratio = 1.59, 1.8 or 2.2.
[f]See footnote g, Table A.

From the results reported in Table 7 above, it can be seen that both MgO and CaHAP catalysts having Ca/P ratios greater than 1.67 produce good results for cracking the BIS/FAM feed, whereas NVF selectivity was significantly lower with the alumina/silica catalyst and

TABLE 6

Cracking of BIS to NVF Using BIS/H2O Feeds

| Run | Catalyst[b,c] | Temp. (°C.) | BIS/H2O[d] (mL/hr) | N2/He (SCCM) | % BIS Conv. | % NVF[e] Select. |
|---|---|---|---|---|---|---|
| 58 | MgO | 210 | 5.0 | 500 | 90 | 66 |
| 59 | MgO | 235 | 5.0 | 500 | 98 | 82 |
| 60 | MgO | 247 | 10.0 | 500 | 96 | 76 |
| 61 | MgO | 265 | 67.7 | 5000 | 99 | 87 |
| 62 | MgO | 280 | 20.0 | 500 | 99 | 73 |
| 63 | MgO | 325 | 10.0 | 500 | 100 | 54 |
| 64 | Darco Carbon | 280 | 5.0 | 500 | 99 | 51 |
| 65 | Darco Carbon | 275 | 9.7 | 700 | 91 | 95 |
| 66 | 13% AS[f] | 250 | 5.0 | 700 | 98 | 61 |
| 67 | gamma-Al2O3 | 250 | 5.0 | 700 | 99 | 13 |

[a]Reactor Pressure = 800–900 torr. BIS purity = 99.6%; feed purged with and maintained under N2 atmosphere.
[b]Catalyst charge was 2.0 cc, 10-16 mesh, in ¼" OD 316 ss reactor tube for all runs except run 61. See footnotes e and f Table 4 for catalyst descriptions.
[c]Run 61 catalyst charge was 13 cc, in a 1" OD 316 ss reactor tube.
[d]Feed = 44.4 wt % BIS in H2O for runs 58 to 64 and 41.9 wt % for runs 58 to 60.
[e]Mole % selectivity = (moles NVF produced/moles BIS consumed)*100. Values given after 4 hrs on stream.
[f]Davison grade 980-13 alumina/silica, Lot No. 980085X1950; surface area = 375 m2/g; NVF selectivity = 24% at 1 hr. onstream.

From the results reported in Table 6 above, it can be seen that good cracking results are obtained when a BIS/H2O feed is reacted in the presence of either MgO or Darco Carbon catalysts. Inferior results were obtained when using 13% AS or gamma - $Al_2O_3$.

EXAMPLE 12

Several runs were carried out in accordance with the general procedure set out in Example 5 above. The feed was 20.0 wt % BIS (99.6% purity) in FAM, and the catalysts used were MgO and calcium hydroxyapatite (CaHAP) having Ca/P ratios from 1.5 to 2.2. As the Ca/P ratio of CaHAP catalysts increase, the hydrogen-abstracting ability also increases, and hence the catalysts become better suited for the cracking process. A the CaHAP catalyst having a Ca/P ratio of 1.59.

EXAMPLE 13

Several runs were carried out in accordance with the general procedure of Example 5 to crack N-(1-ethoxyethyl)formamide (EEF) having a purity of 95.0%. An ethanol (EtOH) diluent was used for several of the runs. The reaction was carried out at a reactor pressure of 800–900 torr, and the EEF or EEF/EtOH feed was purged with and maintained under $N_2$ atmosphere. The catalyst charge was 2.0 cc, 10–16 mesh. Comparative runs 79 and 80 using $Al_2O_3$ and CaHAP having a Ca/P ratio of 1.59 were carried out for the EEF feed, and comparative runs 85-87 using quartz chips, $Al_2O_3$ and $Na_2O/Al_2O_3$, respectively, all of which have cracking index values below 200, were carried out for the EEF-/EtOH feed. The reaction conditions and results of the runs are reported in Table 8 below.

TABLE 8

Cracking of EEF to NVF Using EEF/EtOH Feeds

| Runs | Catalyst | Temp. (°C.) | EEF (mL/hr) | EtOH (mL/hr) | N2/He (SCCM) | % EEF Conv. | % NVF[a] Select. |
|---|---|---|---|---|---|---|---|
| 75 | Darco Carbon[b] | 275 | 4 | 0 | 300 | 86 | 68 |
| 76 | Darco Carbon[b] | 325 | 4 | 0 | 300 | 97 | 79 |
| 77 | Super A[c] | 325 | 4 | 0 | 300 | 99 | 78 |
| 78 | MgO[d] | 325 | 4 | 0 | 300 | 77 | 76 |
| 79 | Al2O3[e] (comparative) | 325 | 4 | 0 | 300 | 99 | 11 |
| 80 | CaHAP-1.59 (comparative) | 250 | 4 | 12 | 900 | 96 | .5 |
| 81 | CaHAP-2.2 | 275 | 4 | 12 | 900 | 96 | 72 |
| 82 | MgO[g] | 275 | 4 | 12 | 900 | 78 | 93 |
| 83 | MgO[h] | 275 | 4 | 12 | 900 | 97 | 29 |
| 84 | Darco Carbon[b] | 275 | 4 | 12 | 900 | 98 | 81 |
| 85 | Quartz Chips[i] (comparative) | 275 | 4 | 12 | 900 | 14 | 52 |
| 86 | Al2O3[e] (comparative) | 250 | 4 | 12 | 900 | 100 | 2 |
| 87 | Na2O/Al2O3[f] (comparative) | 250 | 4 | 12 | 900 | 100 | 3 |

[a]mole % selectivity = (moles NVF produced/moles EEF consumed) 100. Values given after 4 hrs on stream.
[b]Darco granular activated carbon, Lot No. 0909BJ; surface area (SA) = 600 m2/g.
[c]Amoco Super-A carbon, Lot 79-9, sample 332GX31, SA = 3000 m2/g.
[d]Calgon granular MgO, Maglite CG11, SN R-1970, SA = 30 m2/g.
[e]Catapal alumina ⅛" extrudates, Lot 136J131-2C, calcined at 500 C, SA = 211 m2/g.
[f]See [e] above; then base treated with NaOH solution to pH = 9.5 and calcined at 600 C.
[g]Harshaw MgO, MG-0601 T ⅛", S.N. 407A-20-S-10, SA = 20 m2/g.
[h]Calgon granular MgO, Maglite CG10, SN R-1813, SA = 190 m2/g.
[i]19.07 gms, 10-16 mesh, quartz chips total in 9/16" OD reactor tube.

From the results reported in Table 8 above it can be seen that the catalysts of the present invention produced far superior results than the catalyst used in the comparative runs under similar reaction conditions.

EXAMPLE 14

N-(1-acetoxyethyl)formamide (AEF), a viscous liquid, was synthesized and analyzed by $^1H$ NMR. Initial assignment of the spectra was aided by $^{13}C$ NMR spectra and $^{13}C$-$^1H$ heteronuclear correlation experiments. The AEF sample had a purity of 81.8% as determined using a THF internal standard. 2.0 cc of 10-16 mesh Darco carbon catalyst was loaded into a 9/16" OD 316 stainless steel tube with 9.06 g of 10-16 mesh quartz chips pre-bed vaporizer and 8.45 g as post-bed support material. The tube was assembled into a down-flow reactor and heated to 275° C. under a flow of 390 SCCM He. The AEF was then pumped to the heated reactor at a feed rate of 4.0 cc/hr and total pressure of 850 torr. The reactor effluent was cooled and samples collected over a 19 hr period. 20.0 wt % THF was added to the effluent for quantitative analysis and the samples analyzed by $^1H$ NMR. The AEF conversion was 100% and the selectivity to NVF averaged 87.5% after 4 hrs on stream.

EXAMPLE 15

N-(1-ethoxyethyl)acetamide (EEA) was prepared as a viscous liquid and, as analyzed by $^1H$ and $^{13}C$ NMR, had a purity of 98.5%. An ethanolic solution containing 19.8 wt % EEA was prepared by mixing 15.02 g EEA and 60.99 g ethanol. The solution was deoxygenated by purging the headspace of the glass bottle with N2, shaking the capped bottle well, and repeating this procedure. 2.05 cc of Harshaw MgO catalyst was loaded into a 9/16" OD 316 stainless steel tube with 9.08 g of 10-16 mesh quartz chips pre-bed vaporizer and 8.16 g as post-bed support material. The tube was assembled into a down-flow reactor and heated to 275° C. under a flow of 900 SCCM He. The EEA was then pumped to the heated reactor at a flow rate of 16.22 ml/hr and total pressure of 850 torr. The reactor effluent was cooled and samples collected over a 4 hr period. 1.00 g of the effluent was added to 9.00 g methanol and 0.15 g N-methylpyrrolidone for quantitative analysis by gas chromatography. The EEA conversion was 63.3% and the selectivity to N-vinylacetamide (NVA) was 51.8% after 4 hrs on stream.

EXAMPLE 16

The general cracking process in the present invention was carried out to attempt to crack a tertiary amide. N-(methyl)-N-(1-ethoxyethyl)acetamide (NEEA) was prepared, analyzed by NMR, and its purity estimated to be 42%. The other primary component was N-methyl acetamide. An ethanolic solution containing MEEA was prepared by mixing 25.01 g of the MEEA acetamide and 45.0 g ethanol. The solution was deoxygenated by purging the headspace of a glass bottle with N2, shaking the capped bottle well and repeating this procedure. 2.05 cc of Harshaw MgO catalyst was loaded into a 9/16" O.D. 316 ss tube with 10.0 g of 10-16 mesh quartz chips pre-bed vaporizer and 7.4 g as post-bed support material. The tube was assembled into a down-flow reactor and heated to 275° C. under 900 sccm He. The MEEA solution was pumped to the heated reactor at a flow rate of 19.3 ml/hr and total pressure of 850 torr. The reactor effluent was cooled and samples were collected over a four hour period. 1.00 g of the effluent was added to 9.00 g methanol and 0.15 g N-methyl pyrrolidone for quantitative analysis by gas chromatography. The results indicated that there was no MEEA conversion, clearly demonstrating that the process of the present invention is not effective for tertiary amides.

The present invention provides an efficient, low temperature process for vinylic cracking carboxylic acid amides, especially ethylidene bis(formamide), which are vinylamide precursors, to produce N-vinyl amides such a N-vinyl formamide. The present low temperature process is advantageous in that thermal decomposition of formamide to hydrogen cyanide and water is known to occur at temperatures above or about 350° C. (see Kirk-Othmer Encyclopedia of Chemical Technology, 3rd Ed., Vol. 11, p. 258, and also Sennewald, U.S. Pat. No. 3,702,887). Consequently, the process of the present invention, greatly reduces or eliminates, the hazard of HCN production, which is a serious problem with prior, high temperature techniques. For example, analysis of reactor effluents for cyanide after various low temperature (275° C.) runs showed cyanide levels between 0.092–0.129 ppm, whereas at 400° C., cyanide levels of 149 ppm and 3750 ppm were measured for the same reaction using quartz and carbon catalysts respectively. The comparative examples above clearly show that, when run at temperatures of 150°–350° C., the present invention results in far superior conversions and/or selectivities to desired products than prior art processes, when carried out under similar conditions.

Having thus described the present invention what is now deemed appropriate for Letters Patent is set out in the following appended claims.

What is claimed is:

1. In a process for forming N-vinyl amides having the structural formula:

$$CH_2=CH-NHCOR^1$$

wherein $R^1$ is hydrogen, a $C_1$ to $C_6$ alkyl group or a $C_6$–$C_9$ aryl or substituted aryl group, by heating to a temperature of about 210°–350° C., carboxylic acid amides having the structural formula:

$$CH_3-\underset{\underset{R^2}{|}}{CH}-NHCOR^1$$

wherein
   $R^1$ is defined above, and
   $R^2$ is a $C_1$ to $C_9$ alkoxy, carboxy or carboxamide group, the improvement for achieving higher conversions and/or selectivities for said N-vinyl amides which comprises:
   heating said carboxylic acid amides in the presence of a porous catalytically active material selected from the group consisting of: activated carbon, magnesium oxide, strontium pyrophosphate, neutral or basic calcium hydroxyapatite, CuCrO$_2$ and La$_2$O$_3$.

2. A process in accordance with claim 1 wherein ethylidene bis(formamide) is heated to form N-vinyl formamide.

3. A process in accordance with claim 1 wherein said porous catalytically active material is activated carbon.

4. A process in accordance with claim 1 wherein said porous catalytically active material is magnesium oxide.

5. A process in accordance with claim 1 wherein an inert gas is used as a diluent to establish low partial pressure of the organic amide during the vinylic catalytic cracking of the carboxylic acid amides.

6. A process in accordance with claim 5 wherein said inert gas is selected from the group consisting of N$_2$, He and Ar.

7. A process in accordance with claim 5 wherein said inert gas is present in an amount from 20–98 mole % based on feed.

8. A process in accordance with claim 1 wherein said process is carried out at a pressure range of about 3 torr to about 3000 torr.

9. A process in accordance with claim 8 wherein said process is carried out at a pressure of 3 torr to 1000 torr.

10. A process in accordance with claim 1 wherein $R^1$ is H.

11. A process in accordance with claim 1 wherein the carboxylic acid amide is selected from the group consisting of: ethylidene bis(formamide), N-(1-ethoxyethyl)formamide, N-(1-acetoxyethyl)formamide, N-(1-ethoxyethyl)acetamide, N-(1-methoxyethyl)formamide and N-(1-methoxyethyl)acetamide.

12. A process in accordance with claim 1 wherein the carboxylic acid amide is mixed with a functionally inert solvent.

13. A process in accordance with claim 12 wherein said inert solvent is selected from the group consisting of water, ethanol and formamide.

14. A process in accordance with claim 1 wherein said process is carried out as a batch process.

15. A process in accordance with claim 1 wherein said process is carried out as a continuous process in a flow reactor.

16. A process in accordance with claim 1 wherein said process is carried out primarily in the gas phase.

17. A process in accordance with claim 1 wherein said process is carried out at subatmospheric pressure using a vacuum.

18. A process in accordance with claim 1 wherein said process is carried out at atmospheric pressure.

19. A process in accordance with claim 1 wherein oxygen is purged from the organic amide before the amide is fed to the catalyst.

* * * * *